US012690618B2

(12) United States Patent
Zhang

(10) Patent No.: US 12,690,618 B2
(45) Date of Patent: Jul. 28, 2026

(54) ELECTRONIC ATOMIZATION DEVICE AND ATOMIZER AND SEALING STRUCTURE THEREOF, AND ATOMIZER ASSEMBLING METHOD

(71) Applicant: SHENZHEN SMOORE TECHNOLOGY LIMITED, Shenzhen (CN)

(72) Inventor: Xin Zhang, Shenzhen (CN)

(73) Assignee: SHENZHEN SMOORE TECHNOLOGY LIMITED, Shenzhen (CN)

( * ) Notice: Subject to any disclaimer, the term of this patent is extended or adjusted under 35 U.S.C. 154(b) by 522 days.

(21) Appl. No.: 17/531,799

(22) Filed: Nov. 21, 2021

(65) Prior Publication Data

US 2022/0079241 A1 Mar. 17, 2022

Related U.S. Application Data

(63) Continuation of application No. PCT/CN2019/088011, filed on May 22, 2019.

(51) Int. Cl.
*A24F 40/485* (2020.01)
*A24F 40/10* (2020.01)
(Continued)

(52) U.S. Cl.
CPC ............ *A24F 40/485* (2020.01); *A24F 40/10* (2020.01); *A24F 40/42* (2020.01); *B05B 15/65* (2018.02); *A61M 11/02* (2013.01)

(58) Field of Classification Search
CPC .................................................. A24F 40/485
See application file for complete search history.

(56) References Cited

U.S. PATENT DOCUMENTS

2016/0262455 A1 9/2016 Chen
2018/0160738 A1* 6/2018 Verleur .................. A24F 40/48
(Continued)

FOREIGN PATENT DOCUMENTS

CN 203986095 U 12/2014
CN 104872822 A 9/2015
(Continued)

OTHER PUBLICATIONS

International Search Report of PCT Patent Application No. PCT/CN2019/088011 issued on Feb. 19, 2020.
(Continued)

*Primary Examiner* — Michael H. Wilson
*Assistant Examiner* — Courtney G Culbert
(74) *Attorney, Agent, or Firm* — Andrew C. Cheng

(57) ABSTRACT

The present disclosure relates to an an electronic atomization device and an atomizer and a sealing structure thereof, and an atomizer assembling method. The sealing structure includes an elastic annular portion and at least one reinforcement portion. The at least one reinforcement portion is disposed in the annular portion, and two ends of the reinforcement portion are respectively connected with two opposite sides of the annular portion. The sealing structure facilitates automatic assembly and has the advantages of convenient assembly and low assembly cost. The atomizer is provided with the sealing structure of the present disclosure, and thus has the advantages of convenient assembly and low assembly cost. The atomizer assembling method has the advantages of easy operation, high efficiency and low cost.

19 Claims, 12 Drawing Sheets

(51) Int. Cl.
    *A24F 40/42*    (2020.01)
    *B05B 15/65*    (2018.01)
    *A61M 11/02*    (2006.01)

(56)            References Cited

U.S. PATENT DOCUMENTS

| | | | |
|---|---|---|---|
| 2019/0021398 | A1 | 1/2019 | Qiu |
| 2019/0046745 | A1* | 2/2019 | Nettenstrom ........... A24F 40/44 |
| 2020/0069894 | A1* | 3/2020 | Qiu ......................... A24F 40/49 |

FOREIGN PATENT DOCUMENTS

| | | | |
|---|---|---|---|
| CN | 105394816 | A | 3/2016 |
| CN | 105433443 | A | 3/2016 |
| CN | 105433443 | U | 3/2016 |
| CN | 205305989 | U | 6/2016 |
| CN | 205321208 | U | 6/2016 |
| CN | 205337599 | U | 6/2016 |
| CN | 205585319 | U | 9/2016 |
| CN | 106136328 | A | 11/2016 |
| CN | 205757197 | U | 12/2016 |
| CN | 206005949 | U | 3/2017 |
| CN | 206284403 | U | 6/2017 |
| CN | 206433758 | U | 8/2017 |
| CN | 107156912 | A | 9/2017 |
| CN | 107580460 | A | 1/2018 |
| CN | 107635418 | A | 1/2018 |
| CN | 206923668 | U | 1/2018 |
| CN | 107684109 | A | 2/2018 |
| CN | 108185536 | A | 6/2018 |
| CN | 108308716 | A | 7/2018 |
| CN | 207613191 | U | 7/2018 |
| CN | 108354235 | A | 8/2018 |
| CN | 207855040 | U | 9/2018 |
| CN | 208160039 | U | 11/2018 |
| CN | 109007980 | A | 12/2018 |
| CN | 208259011 | U | 12/2018 |
| CN | 109198728 | A | 1/2019 |
| CN | 109315839 | A | 2/2019 |
| CN | 208490850 | U | 2/2019 |
| CN | 109393569 | A | 3/2019 |
| CN | 109527657 | A | 3/2019 |
| CN | 208798694 | U | 4/2019 |
| CN | 209284320 | U | 8/2019 |
| CN | 210382635 | U | 4/2020 |
| CN | 210382636 | U | 4/2020 |
| CN | 210445695 | U | 5/2020 |
| CN | 212899691 | U | 4/2021 |
| EP | 2614731 | A1 | 7/2013 |
| FR | 2642808 | A1 | 8/1990 |
| JP | S59201730 | A | 11/1984 |
| WO | 2015010278 | A1 | 1/2015 |
| WO | 2015051538 | A1 | 4/2015 |
| WO | 2016/045084 | A1 | 3/2016 |
| WO | 2018024213 | A1 | 2/2018 |
| WO | 2018094564 | A1 | 5/2018 |
| WO | 2018126425 | A1 | 7/2018 |
| WO | 2018223290 | A1 | 12/2018 |

OTHER PUBLICATIONS

Notice of correction of CN application No. 201920747505.2 issued on Mar. 6, 2022.
Notice of correction of CN application No. 201920745343.9 issued on Mar. 9, 2022.
The extended European search report of EP application No. 19929824.1 issued on Mar. 25, 2022.
Search Report of CN application No. 201910430388.1 issued on Jun. 16, 2023.
The First Office Action of CN application No. 201910430388.1 issued on Jun. 16, 2023.
The First Office Action of EP application No. 19929824.1 issued on Jun. 6, 2023.
International Written Opinion of PCT Patent Application No. PCT/CN2019/088011 issued on Feb. 19, 2020.
The second Office Action of CN patent application No. 201910430388.1 issued on Feb. 3, 2024.
The first Office Action of CN patent application No. 201910430383.9 issued on Dec. 26, 2023.
The search report of CN patent application No. 201910430383.9 issued on Dec. 26, 2023.
The first Office Action of CN patent application No. 201910430397.0 issued on Dec. 25, 2023.
The search report of CN patent application No. 201910430397.0 issued on Dec. 25, 2023.
The Office Action of EP patent application No. 19929824.1 issued on May 19, 2026.

\* cited by examiner

100

20

ELECTRONIC ATOMIZATION DEVICE AND ATOMIZER AND SEALING STRUCTURE THEREOF, AND ATOMIZER ASSEMBLING METHOD

TECHNICAL FIELD

The present disclosure relates to an atomization device, more particularly, to an electronic atomization device and an atomizer and a sealing structure thereof, and an atomizer assembling method.

BACKGROUND

With the development of society, in the field of industrial production, especially in the field of electronic atomization device production, mechanical automatic assembly has gradually replaced manual assembly. When assembling an atomizer, some sealing structures are generally used to seal the atomizer. The sealing structure, which is generally a silicon rubber ring or a rubber ring, does not have a reinforcing structure on an inner side thereof. Thus when the sealing structure is picked up to a base or other component of the atomizer by a manipulator, elastic deformation is easily produced, and the sealing structure is difficult to be accurately sleeved on the base or other component, so that the automatic production can not be facilitated smoothly, and the automatic production need to be interrupted for a manual adjustment, and it is easy to cause the increase of product defect rate.

SUMMARY

A technical problem to be solved by the present disclosure is to provide an improved sealing structure, and further provide an atomizer, an electronic atomization device and an atomizer assembling method.

A technical solution adopted by the present disclosure to solve the technical problem is to provide a sealing structure, including an elastic annular portion and at least one reinforcement portion; wherein the at least one reinforcement portion is disposed in the annular portion and two ends of the reinforcement portion are connected to two opposite sides of the annular portion respectively.

Preferably, the at least one reinforcement includes at east two reinforcement portions;

the at least two reinforcement portions are arranged separately and side by side, and two ends of each reinforcement portion are respectively connected with two opposite sides of the annular portion;

or alternatively, the at least two reinforcement portions are arranged crosswise, and two ends of each of the reinforcement portions are respectively connected to two opposite sides of the annular portion.

Preferably, the sealing structure further includes a pickup portion cooperating a picker; and the pickup portion is disposed on an inner side of the annular portion and is connected with the annular portion through the reinforcement portion.

Preferably, the reinforcement portion, the pickup portion and the annular portion are integrally formed.

Preferably, the pickup portion includes a cylindrical body and at least one pickup hole; and the at least one pickup hole is defined in the cylindrical body.

Preferably, the pickup hole includes a strip-shaped hole; and an isolation portion is arranged between the periphery of the strip-shaped hole and the inner side wall of the cylindrical body.

Preferably, a collecting cativy is defined inside the cylindrical body for converging airflow and outputting the airflow through the pickup hole.

Preferably, the annular portion has an elliptical shape; the strip-shaped hole is disposed in a long axis direction of the annular portion and extends in the long axis direction of the annular portion.

The disclosure further provides an atomizer which includes a base, a cartridge sleeved on a periphery of the base, an atomization assembly disposed in the cartridge and the sealing structure of the present disclosure; and the sealing structure is sleeved on the base and disposed between the base and the cartridge.

Preferably, the annular portion of the sealing structure is sleeved on the base and located between the base and the cartridge.

Preferably, the base includes a base body; and the base body is provided with an air inlet passage; and the sealing structure includes a pickup portion disposed on an inner side of the annular portion; the pickup portion is disposed at an outlet end of the air inlet passage.

Preferably, the pickup portion includes a cylindrical body and a pickup hole defined in the cylindrical body;

a shape and a dimension of the cylindrical body are matched with a shape and a dimension of the air inlet passage; and the pickup hole is communicated with the air inlet passage to form an air outlet hole.

Preferably, the outlet end of the air inlet passage is provided with an isolation mesh to prevent liquid from leaking out of the air inlet passage.

Preferably, the base further includes a limiting boss disposed on the base body (11) for the annular portion to sleeve; and;

the limiting boss is provided with an interference-preventing notch for giving place to the reinforcement portion.

Preferably, the atomizer further includes an atomization housing disposed on the base; and the atomization housing include a sleeve;

the sealing structure is disposed between the base and the sleeve; and the annular portion include a first sleeve portion, a second sleeve portion and a sealing portion; the first sleeve portion is sleeved on the base; the second sleeve portion is disposed at an inner side of the sleeve for sleeving the sleeve; the sealing portion is disposed between the first sleeve portion and the second sleeve portion so as to seal a space between the base and the cartridge.

Preferably, an outer dimension of the sealing portion is larger than outer dimensions of the first sleeve portion and the second sleeve portion.

Preferably, a liquid storage cavity is defined inside the cartridge; the sealing structure is disposed between the sleeve and the liquid storage cavity; and;

the annular portion of the sealing structure is sleeved on an outer periphery of the sleeve.

The disclosure further provides an electronic atomization device which includes a power supply device and the atomizer.

The disclosure further provides an atomizer assembling method, which is applied to the assembly of the atomizer of the disclosure; characterize by including the following steps:

inserting a picker from a pickup hole of a pickup portion of the sealing structure, taking the sealing structure to the base of the atomizer, and sleeving one end of the annular portion of the sealing structure on an outer periphery of the base;

mounting the atomization assembly into a sleeve, inserting the base assembled with the sealing structure into the sleeve, and sleeving the sleeve on another end of the annular portion of the sealing structure;

mounting the base, the sleeve, the sealing structure and the atomization assembly into the cartridge.

The electronic atomization device and the atomizer and the sealing structure thereof, and the atomizer assembling method according to the disclosure have the following beneficial effects: according to the sealing structure, at least one reinforcement portion is disposed in the annular portion, and two ends of the at least one reinforcement portion are respectively connected with two opposite sides of the annular portion, thereby the rigidity of the annular portion is increased, and the deformation of the annular portion during taking and placing is reduced, so that the automatic assembly is facilitated, and the annular portion has the advantage of convenient assembly and low assembly cost.

The atomizer has the advantages of convenient assembly and low assembly cost by providing with the sealing structure of the disclosure.

The electronic atomization device has the advantages of convenient assembly and low assembly cost by providing with the atomizer of the disclosure.

The atomizer assembling method has the advantages of simple and convenient operation, high efficiency and low cost.

BRIEF DESCRIPTION OF THE DRAWINGS

The disclosure will be further described with reference to the accompanying drawings and specific embodiments. In the drawings.

4

Figure 1:
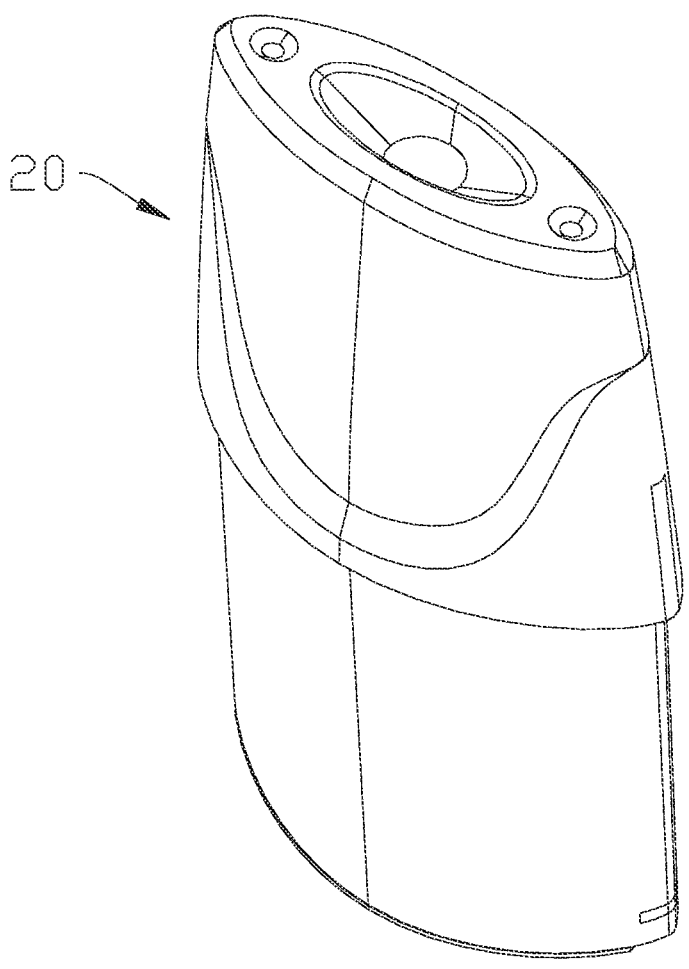
FIG. 1 is a schematic perspective view of an atomizer in some embodiments of the present disclosure.
Figure 14:
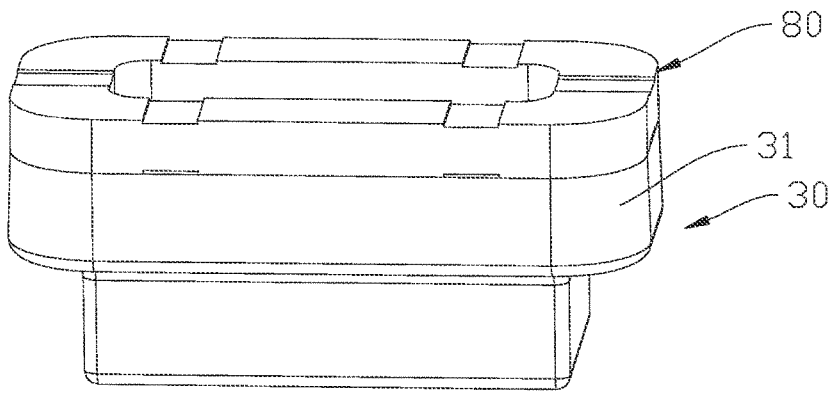
Figure 15:
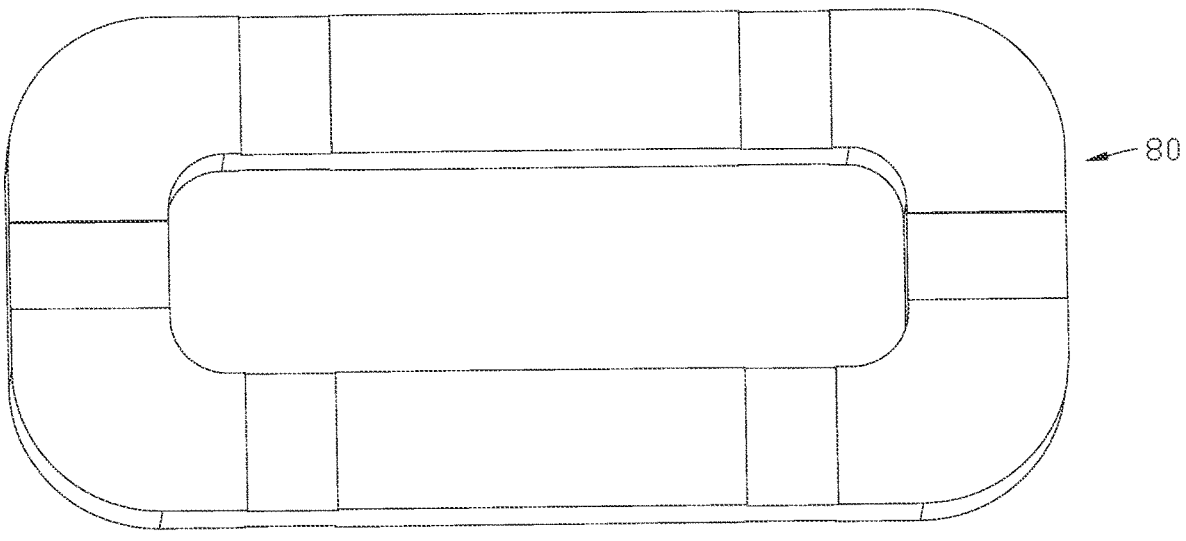
Figure 16:
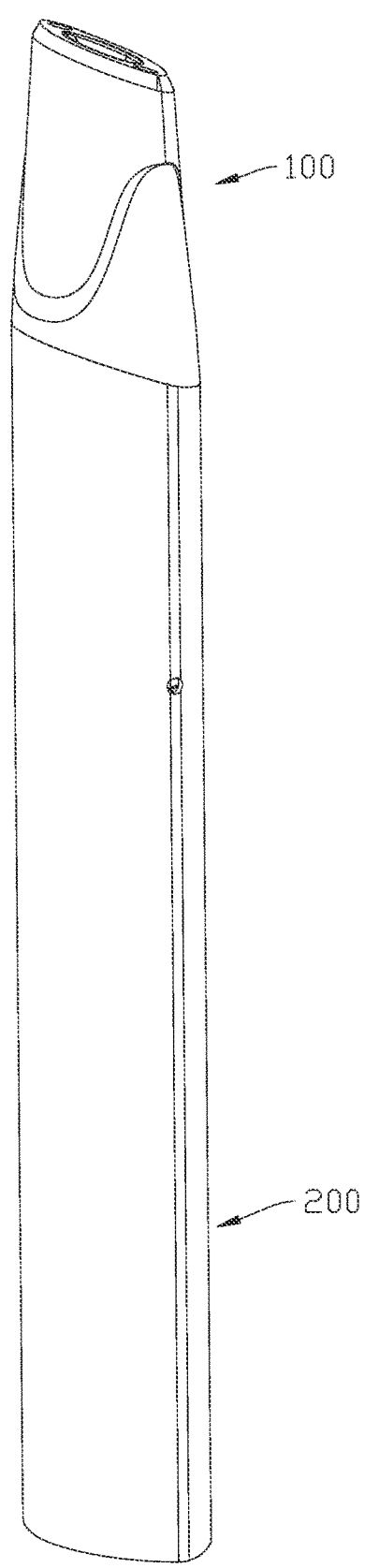
Figure 17:
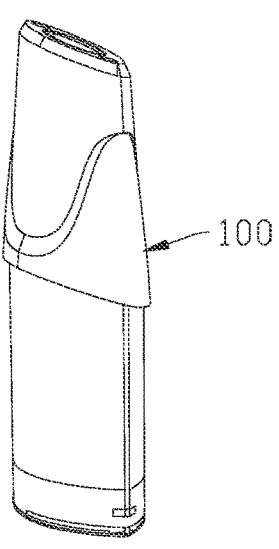
Figure 17:
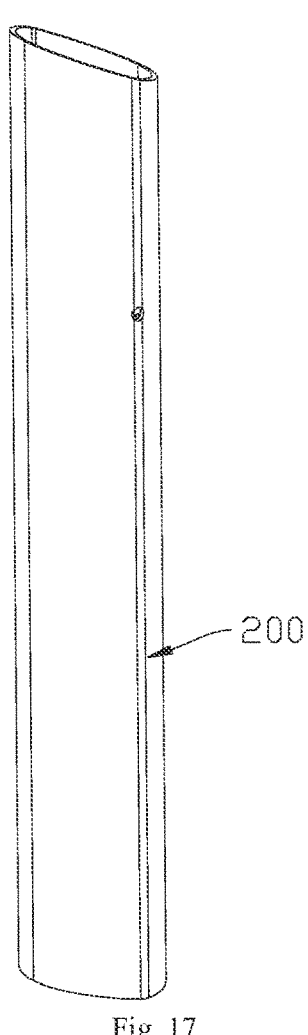

FIG. 14 is a schematic view showing the matching state of the atomization assembly and an elastic member of the atomizer shown in FIG. 1;

FIG. 15 is a schematic structural view of the elastic member of the atomizer shown in FIG. 14;

FIG. 16 is a schematic perspective view of an electronic atomization device in some embodiments of the present disclosure; and FIG. 17 is an exploded view of an atomizer and a power supply device of the electronic atomization device shown in FIG. 16.

PREFERRED EMBODIMENTS

To clearly understand the technical features, objectives and effects of the disclosure, the specific embodiments of the disclosure will now be described in detail with reference to the accompanying drawings.

Figure 2:
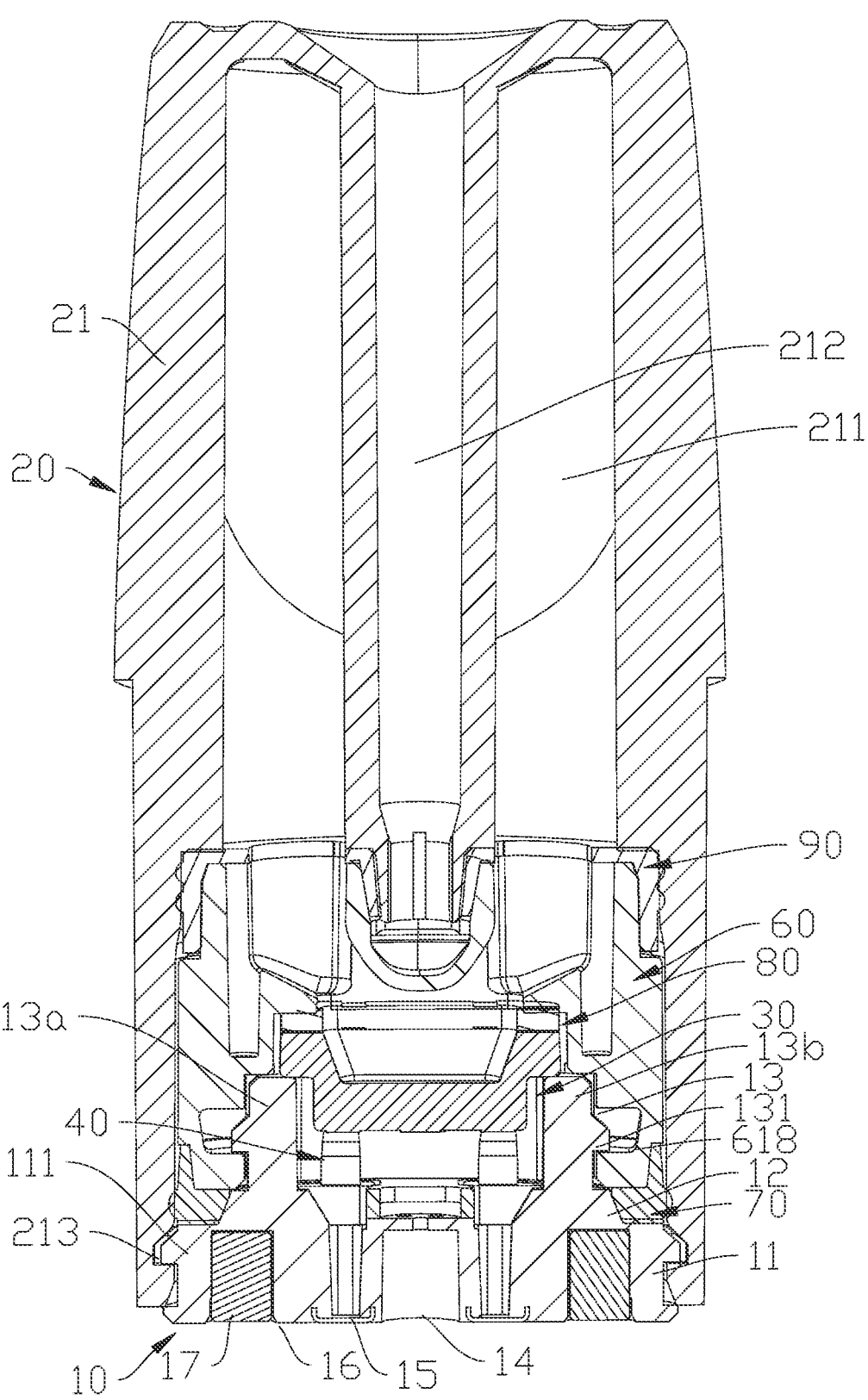
FIG. 2 is a longitudinal sectional view of the atomizer shown in FIG. 1.

FIG. 1 and FIG. 2 show an atomizer 100 in some embodiments of the present disclosure. The atomizer 100 can be used in the field of an electronic cigarette, a medical atomization or the like, and has specific structural characteristics so that an automatic installation method can be conveniently adopted, thereby simplifying the installation process, improving the assembly efficiency, saving the labor cost during assembly, and avoiding some human errors during assembly.

Figure 3:
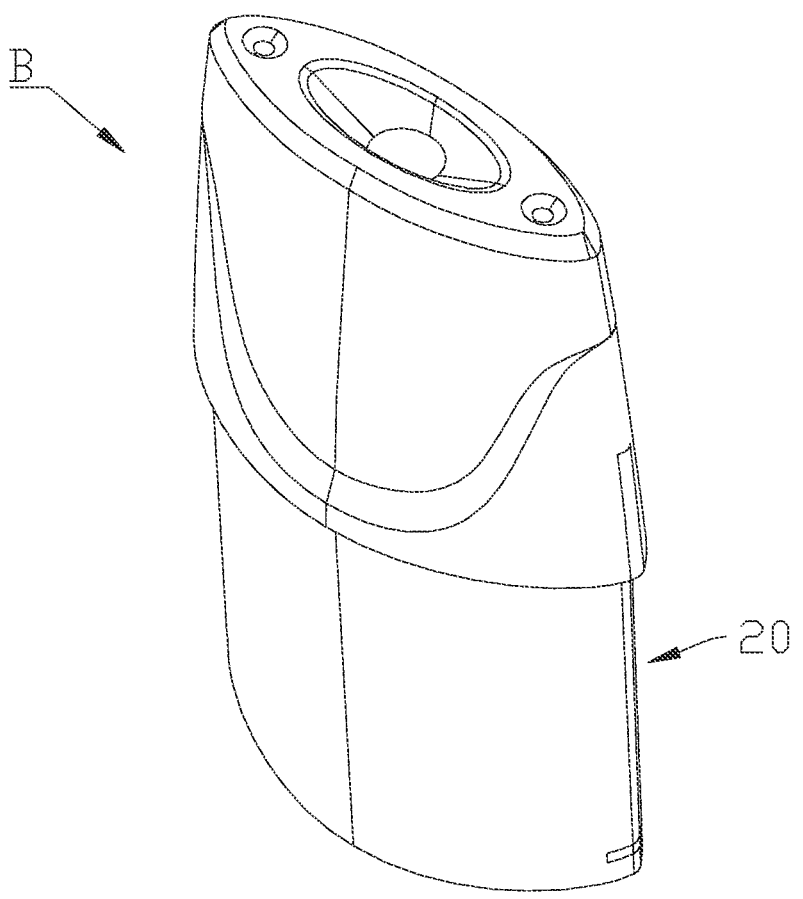
FIG. 3 is an exploded view of an atomization unit A and a liquid storage unit B of the atomizer shown in FIG. 1.
Figure 3:
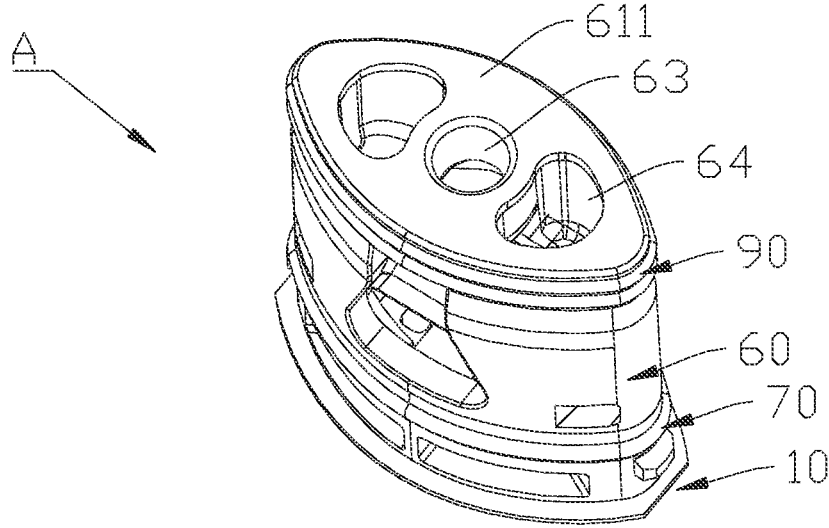
Figure 4:
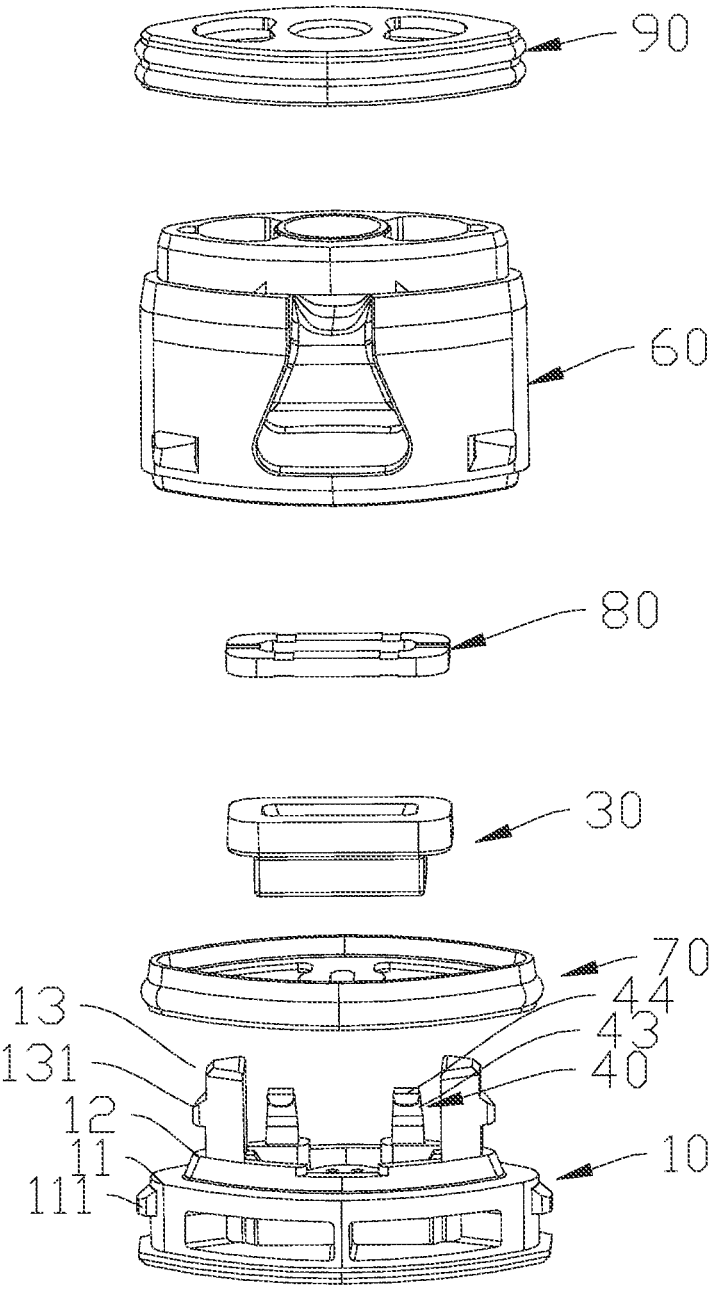
FIG. 4 is an exploded view of the internal components of the atomizer shown in FIG. 3.

As shown in FIG. 3, in some embodiments, the atomizer 100 may include an atomization unit A and a liquid storage unit B sleeved on the atomization unit A, and the liquid storage unit B is fluidly connected with the atomization unit A. The atomization unit A can be used for heating and atomizing a liquid medium, and the liquid storage unit B is used for storing the liquid medium and transferring out aerosol.

As further shown in FIG. 2, the atomization unit A in some embodiments may include a base 10, an atomization assembly 30, two first conductive members 40, two second conductive members 50 and an atomization housing 60. The base 10 in some embodiments may be in an oval shape, and may be used to mechanically and electrically connect with a power supply device 200, and the base 10 may include a base body 11. The atomization assembly 30 is arranged on the base 10, and is disposed corresponding to the base 11. The two first conductive members 40 are spaced disposed on the base 11, and the two second conductive members 50 are spaced disposed on the atomization assembly 30 and abutted with the two first conductive members 40 respectively, so as to form a conductive connection therebetween. The atomization housing 60 is sleeved on the base 10 from top to bottom and covers the atomization assembly 30. The atomization housing 60 may include an integrally formed sleeve, and the sleeve may be sleeved on the base 10 to receive the atomization assembly 30 and form an atomizing chamber 132.

The atomization unit A in some embodiments may further include a sealing structure 70 and an elastic member 80. The sealing structure 70 is disposed between an open periphery of the atomization housing and the base 10. The elastic member 80 is disposed between a top portion of the atomization assembly 30 and the atomization housing, so that the atomization housing is elastically abutted against the top portion of the atomization assembly 30.

Figure 5:
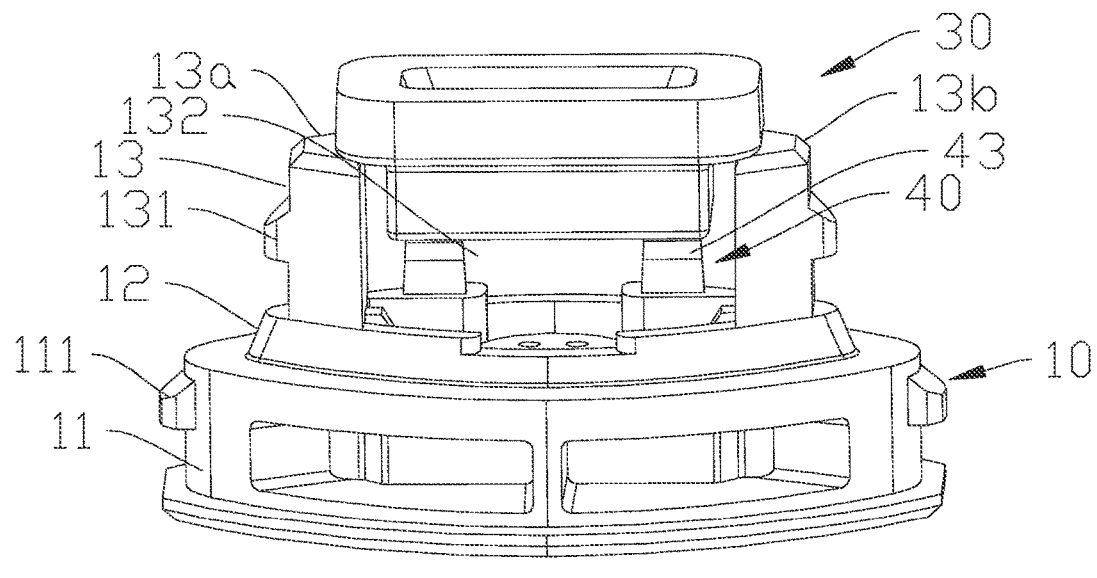
FIG. 5 is a schematic view of a first conductive member on a base in abutting contact with a second conductive member on an atomization assembly of the atomizer shown in FIG. 1.
Figure 6:
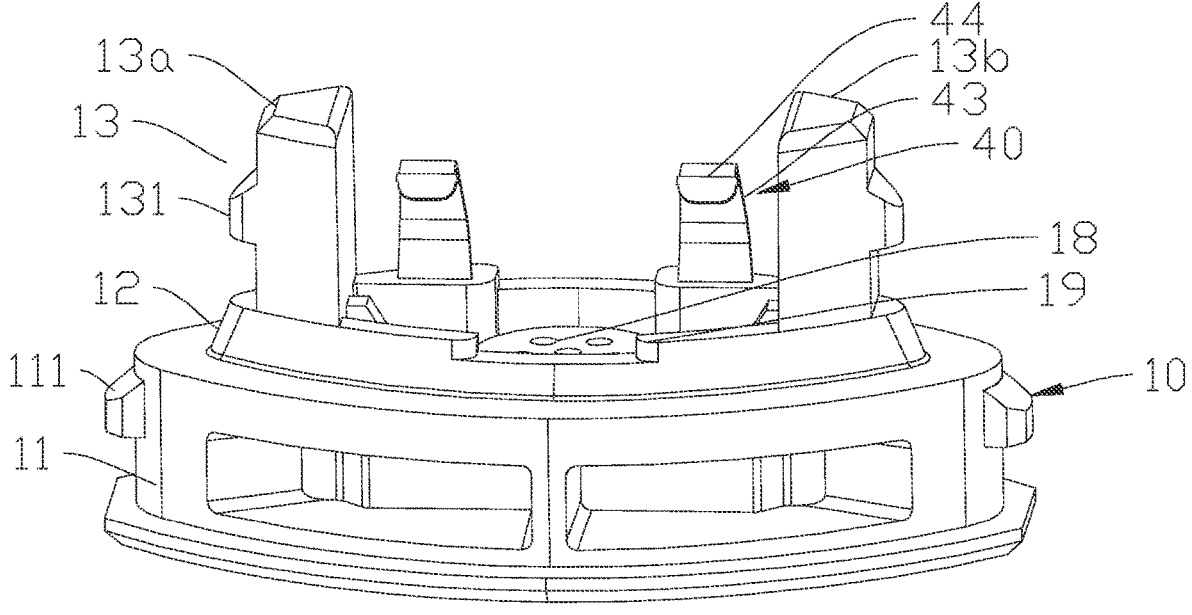
FIG. 6 is a schematic view showing the matching state of the base and the first conductive member of the atomizer shown in FIG. 5.
Figure 7:
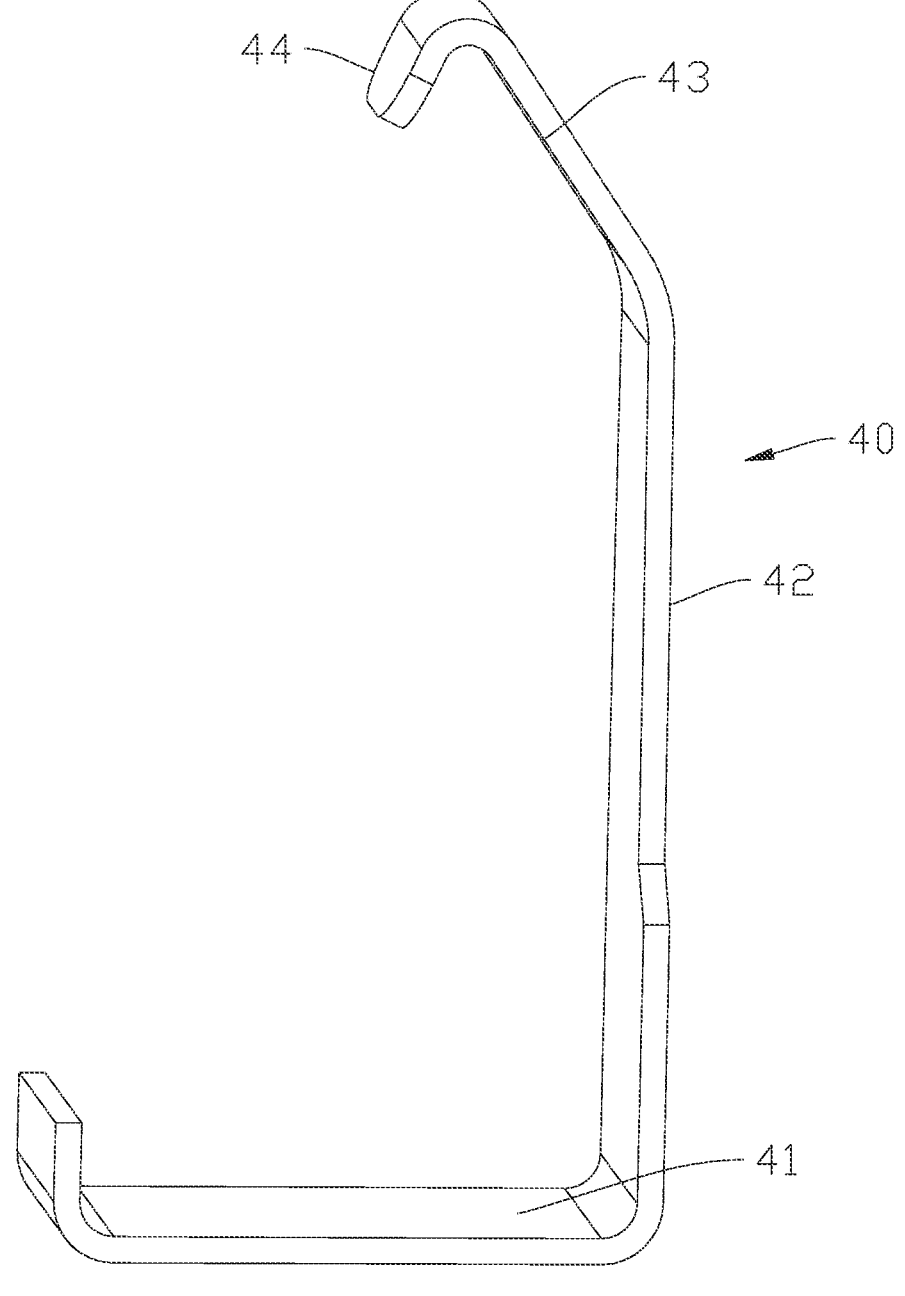
FIG. 7 is a perspective view of the first conductive member of the atomizer shown in FIG. 1.

As shown in FIGS. 5 to 6, the base 10 may include a base body 11, a limiting boss 12, and a set of supporting structure 13. A shape and a dimension of a cross section of the base body 11 are matched with a shape and a dimension of a cross section of a cartridge 20, and the base body 11 can be inserted into the cartridge 20. The limiting boss 12 is disposed on the base 11, and is located on a side of the base 11 towards the atomization assembly 30, and can limit a position of the sealing structure 70. The at least one set of supporting structure 13 is disposed on the base 11, specifically, in this embodiment, is disposed on the limiting boss 12, and can be integrally formed with the limiting boss 12 and the base 11, and can be inserted in the sleeve, and is configured for supporting the atomization assembly 30.

In some embodiments, a shape and a dimension of a cross section of the base body 11 is adapted to a shape and a dimension of a cross section of the cartridge 20, so as to facilitate the installation of the base body 11 in the cartridge 20. Two opposite side walls of the base 11 can be respectively provided with a buckle 111, and the buckle 111 can be clamped into a buckling groove 213 disposed on an inner side wall of a lower portion of the cartridge 20, so that the base 11 can be matched and fixed with the cartridge 20.

In some embodiments, the supporting structure 13 may include two supporting pillars 13a and 13b spaced side by side. The two supporting pillars 13a and 13b may be respectively inserted into the sleeve to support the atomization assembly 30 and be matched and fixed with the sleeve, and a space therebetween may form an atomizing chamber 132. In some embodiments, each supporting structure 13 is provided with hooks 131, and the hooks 131 can be disposed on each supporting pillars 13a and 13b, and located on sides of the supporting pillars 13a, and 13b facing to the cartridge 20. The hook 131 can be engaged with a clamping position 618 provided on an inner side of the sleeve to fix the base 10 in the sleeve.

In some embodiments, the base 11 is provided with an air inlet passage 14, and the air inlet passage 14 is axially arranged in the base 11. A space is defined between the base 11 and the atomization assembly 30 to form the atomizing chamber 132, and the air inlet passage 14 is communicated with the atomizing chamber 132 and configured for allowing air to enter the atomizing chamber 132. In some embodiments, an outlet end of the air inlet passage 14 is provided with a number of isolation meshes 18, and the number of isolation meshes 18 can be used for preventing the liquid medium from leaking out from the air inlet passage 14. When the liquid medium drops on the isolation mesh 18, due to a small aperture of a mesh hole, the liquid medium can form a layer of liquid film in each mesh hole, thereby preventing the liquid medium from leaking out. The base 11 is further provided with at least one demoulding hole 15, and the at least one demoulding hole 15 is arranged at two sides of the air inlet passage 14, which can facilitate the demoulding of the base 11. The at least one demoulding hole 15 can also be used as a liquid storage hole so as to store the leaked liquid. A mounting hole 16 is further defined in the base 11 for mounting a magnet column 17 therein, so that the base 11 can be disposed on the power supply device 200 by magnetic attraction.

Referring to FIGS. 1 and 2, in some embodiments, the liquid storage unit B may include a cartridge 20. The cartridge 20 can be sleeved on the base 10, and an inner side of the cartridge 20 can be configured for forming a liquid storage cavity for storing the liquid medium. The cartridge 20 may include a shell body 21 and a ventilation pipe 212. A cross-sectional shape of the shell body 21 may be elliptical, of course, it can be understood that in other embodiments, the cross-sectional shape of the shell body 21 may not be limited to elliptical. An inner side of the shell body 21 may define a liquid storage cavity 211, and the liquid storage cavity 211 is disposed at an upper portion of the sleeve and is communicated with the sleeve, and may be located at an outer periphery of the ventilation pipe 212. The ventilation pipe 212 is arranged in the shell body 21 and is arranged along an axial direction of the shell body 21. The ventilation pipe 212 is communicated with the sleeve so as to output the aerosol in the sleeve, and is provided with an air outlet at one end far away from the sleeve, and the air outlet can form a suction nozzle for a user to smoke. The air outlet can be provided with a blocker to block the air outlet when the atomizer 100 is not used, so as to prevent impurities from entering the ventilation pipe 212.

Referring to FIGS. 2 to 5 and FIGS. 8 to 9, the atomization assembly 30 may be disposed correspondingly to the base 10 and may be received in the sleeve. The atomization assembly 30 includes a porous body 31 and a heating element 32. The porous body 31 may be disposed correspondingly to the base 10, and may be used for adsorbing liquid. The heating element 32 may be disposed on the porous body 31, and may be used to heat the liquid medium in the porous body 31 to generate aerosol.

In some embodiments, the porous body 31 is spaced from the base 11, and may be supported by the supporting structure 32. A space between the porous body 31 and the base 11 may form the atomizing chamber 132. In some embodiments, a height of the atomizing chamber 132 may be 2 to 2.5 mm. The porous body 31 may be made of a rigid material, in particularly, the porous body 31 may be a ceramic porous body, and can be used to absorb and store a liquid medium, and in some embodiments, a height of the porous body may be 3.3 to 3.5 mm. In this embodiment, the porous body 31 includes an atomizing surface 311 and a liquid adsorbing groove 312. The atomizing surface 311 is defined on a surface of the porous body 31 towards the base 10 and can be used for disposing the heating element 32 thereon. The liquid adsorbing groove 312 is defined on a surface opposite to the atomizing surface 311, and an inner side wall of the liquid adsorbing groove 312 can define a liquid adsorbing surface. The liquid adsorbing groove 312 is communicated with the liquid storage cavity 211, and can be used for receiving the liquid medium so as to facilitate the absorption of the liquid medium by the porous body 31.

The heating element 32 may be in a sheet shape, may be tiled on the atomizing surface 311, and may be integrally formed with the porous body 31 by sintering. In some embodiments, the atomizing surface 311 may be further provided with a receiving groove, and the heating element 32 can be disposed in the receiving groove. In this embodiment, the heating element 32 can be a thin metal sheet, and is elongated, and can be disposed along a length direction of the porous body 31 so as to allow all or most of the surface area of the heating element 32 to be in contact with the porous body 31, thereby improving atomization efficiency and reducing heat loss. In this embodiment, the heating element 32 may be S-shaped, which can make the heat distribution more uniform. Of course, it can be understood that in other embodiments, the heating element 32 is not limited to be designed in an S shape, and can be designed in other shape such as a straight strip shape, a tape rule shape, a wave shape or the like according to needs.

As shown in FIGS. 4 to 7, in some embodiments, the first conductive member 40 can be elongated, and can be disposed on the base 10. It can be understood that the first conductive member 40 can alternatively be disposed on the atomization assembly 30. The first conductive member 40 can be an elastic conductive member that can elastically abut against the second conductive member 50. In some embodiments, the number of the first conductive member 40 may be one or more, which is not limited to two. In this embodiment, the two first conductive members 40 are spaced apart from each other on the base 10, and form an integral structure with the base 10, and respectively extend toward a direction of the atomization assembly 30, so as to reduce the number of assembly components, reduce the installation steps, reduce production and assembly costs, facilitate automated assembly, and improve efficiency. In some embodiments, the first conductive member 40 may be an elastic conductive sheet. It can be understood that in some other embodiments, the first conductive member 40 may not be limited to a sheet shape, it may alternatively be a pillar shape or other shape. The first conductive member 40 can be made of gold plated stainless steel. Since gold is an inert metal, and can be prevented from being oxidized, thereby reducing the harm.

In some embodiments, the first conductive member 40 may include a transverse connecting portion 41, a main portion 42, an abutting portion 43, and a guide portion 44. The transverse connecting portion 41, the main portion 42, the abutting portion 43 and the guide portion 44 are integrally connected to form an integral structure.

The transverse connecting portion 41 may be coupled with one of the base 10 and the atomization assembly 30. In this embodiment, the transverse connecting portion 41 may be disposed on the base 10, and may be integrally formed with the base 10 by injection molding. The base 10 may be provided with a through hole for allowing the transverse connecting portion 41 to be electrically connected to the power supply device. It can be understood that, in other embodiments, the transverse connecting portion 41 may be integrally formed with the porous body 31 by sintering, and may be disposed on the atomizing surface 311 and connected to the heating element 32, and may be integrally formed with the heating element 32.

The main portion 42 may be disposed perpendicular to the transverse connecting portion 41 and may extend through one of the base 10 and the atomization assembly 30. In this embodiment, the main portion 42 may extend through the base 10 and be disposed parallel to the supporting structure 13. Of course, it can be understood that in some other embodiments, the main portion 42 is not limited to being perpendicular to the transverse connecting portion 41, and is not limited to being disposed on the base 10, and can be disposed on the porous body 31 and perpendicular to the atomizing surface 311 of the porous body 31, and the main portion 42 can be used for supporting the abutting portion 43.

The abutting portion 43 can be disposed at an end of the main body 42 away from the transverse connecting portion 41, and can be disposed obliquely towards one side, and can abut against the second conductive member 50. When the first conductive member 40 is inserted into the sleeve and pressed into the base 10, the abutting portion 43 can be elastically deformed by inclining to one side towards the main portion 42, so that the contact area between the abutting portion 43 and the second conductive member 50 can be increased, and the first conductive member 40 and the second conductive member 50 are in good contact with each other, thereby improving the conduction efficiency. As the second conductive member 50 on the atomizing surface may be uneven due to that the atomizing surface of the porous body may be uneven, or the first conductive member 40 may be uneven during injection molding of the first conductive member 40 and the base, thereby a contact between the first conductive member 40 and the second conductive member

50 may be poor. By tilting the abutting portion 43, the first conductive member 40 and the second conductive member 50 can be in good contact with each other. In this embodiment, the abutting portions 43 of the two first conductive members 40 can be inclined towards a same direction, so as to facilitate the demoulding of the base 10. It can be understood that in other embodiments, the abutting portions 43 of the two first conductive members 40 may alternatively be inclined towards opposite directions, as long as it can form a good contact with the second conductive member 50.

The guide portion 44 can be disposed at an end of the abutting portion 43, and can be inclined toward one of the base 10 and the atomization assembly 30, and can guide the deformation direction of the abutting portion 43. The guide portion 44 can also contact the second conductive member 50 to form an electrical conduction. In this embodiment, the guide portion 44 can be inclined toward the base 10, so that one end portion of the guide portion 44 connected with the abutting portion 43 can abut against the second conductive member 50, thereby the abutting area is increased to improve the contact stability. It can be understood that in other embodiments, the guide portion 44 may be omitted. In this embodiment, the two guide portions 44 of the two first conductive members 40 can be inclined toward a same direction, so as to facilitate the demoulding of the base 10. It can be understood that in other embodiments, the two guide portions 44 of the two first conductive members 40 may alternatively be inclined toward opposite directions.

Figure 8:
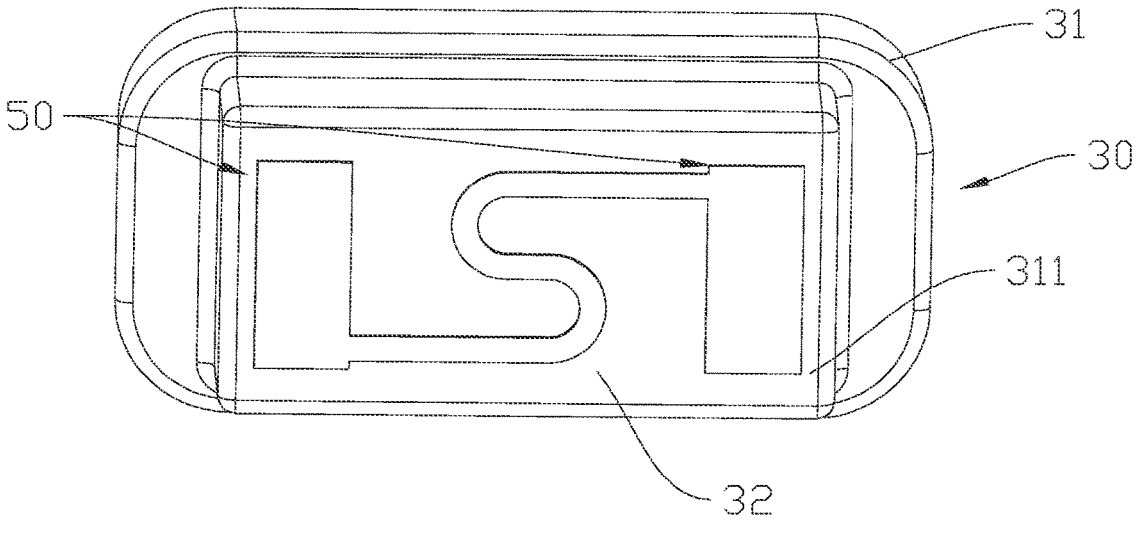
FIG. 8 is a bottom view of the atomization assembly of the atomizer shown in FIG. 1.
Figure 9:
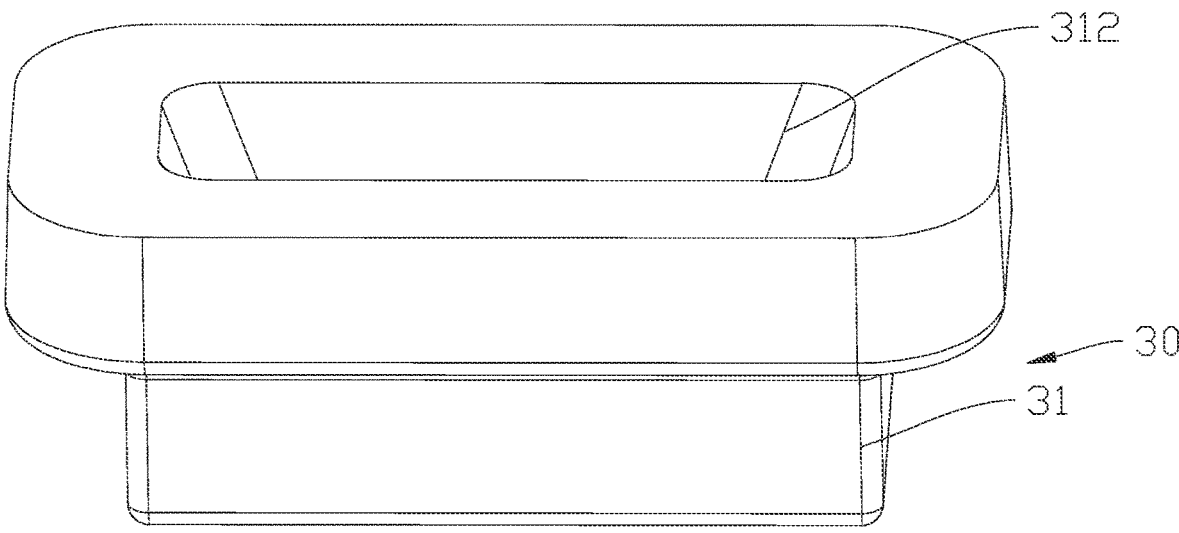
FIG. 9 is a schematic perspective view of the atomization assembly of the atomizer shown in FIG. 1.
Figure 10:
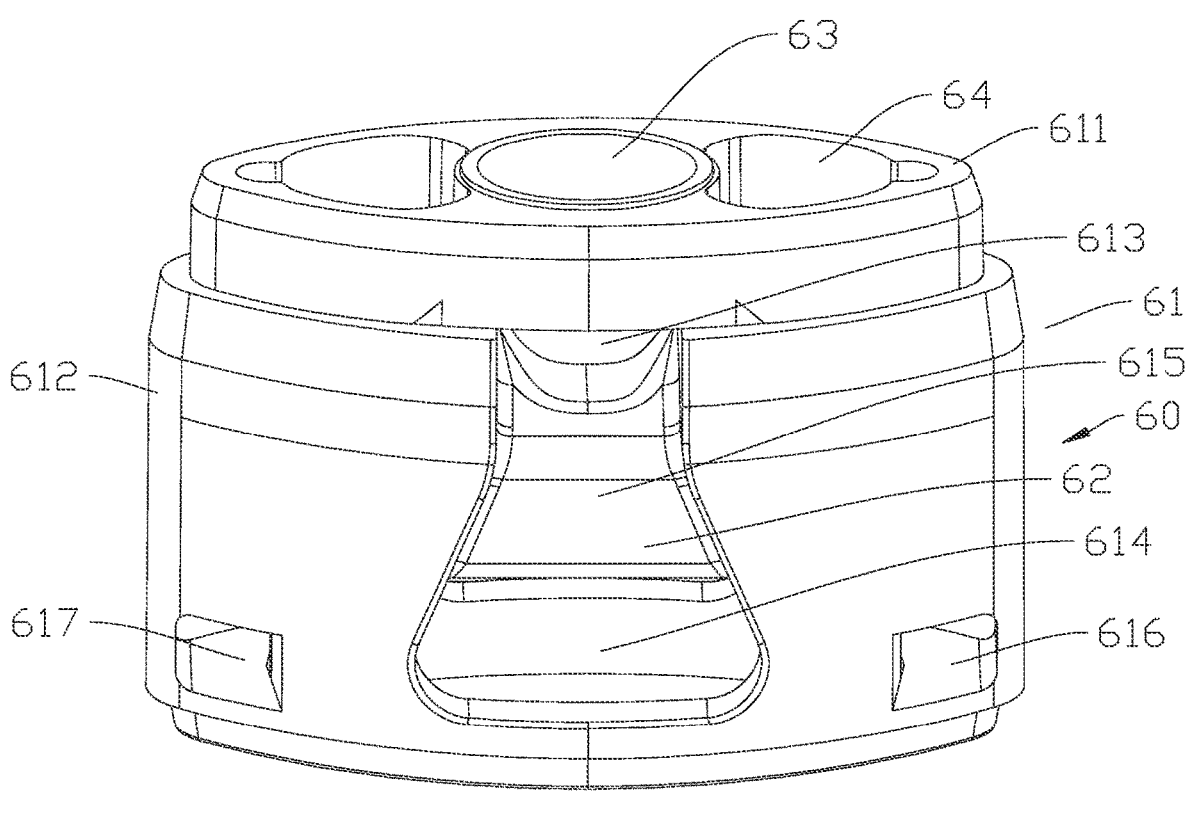
FIG. 10 is a perspective view of a sleeve of the atomizer shown in FIG. 1.
Figure 11:
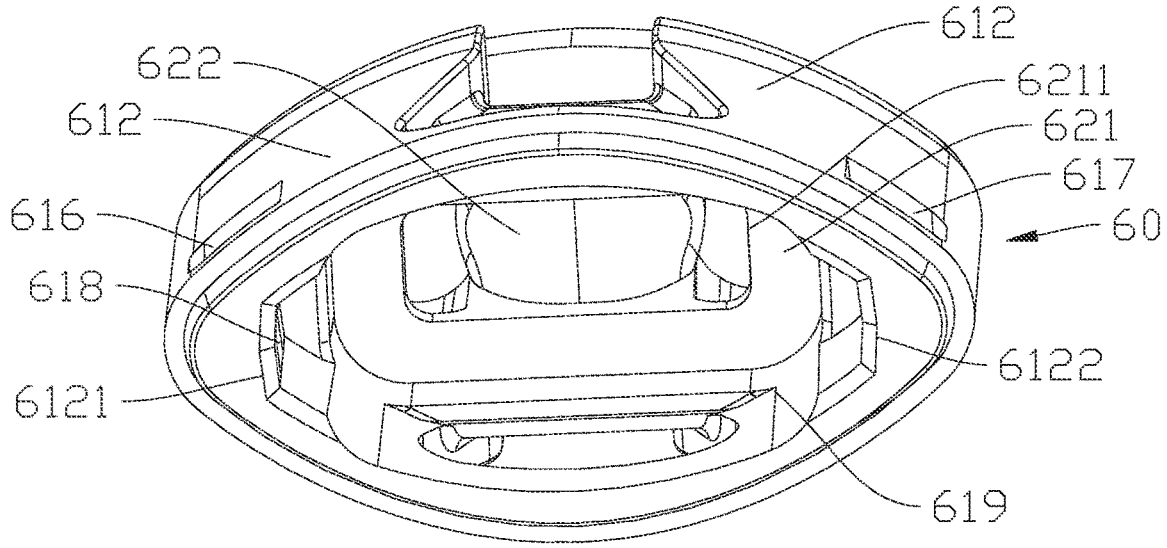
FIG. 11 is a schematic view of the internal structure of the atomizer shown in FIG. 10.
Figure 12:
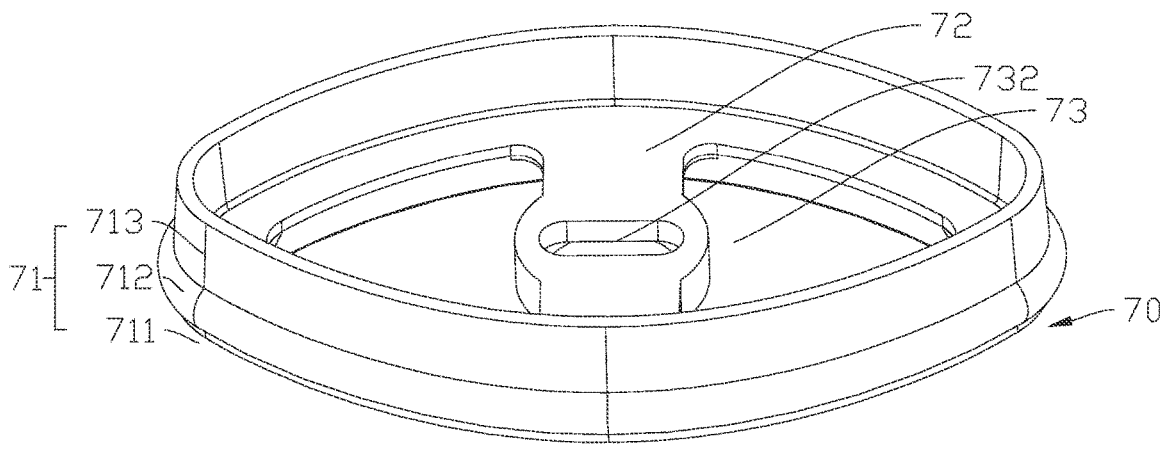
FIG. 12 is a perspective view of a sealing structure of the atomizer shown in FIG. 1.
Figure 13:
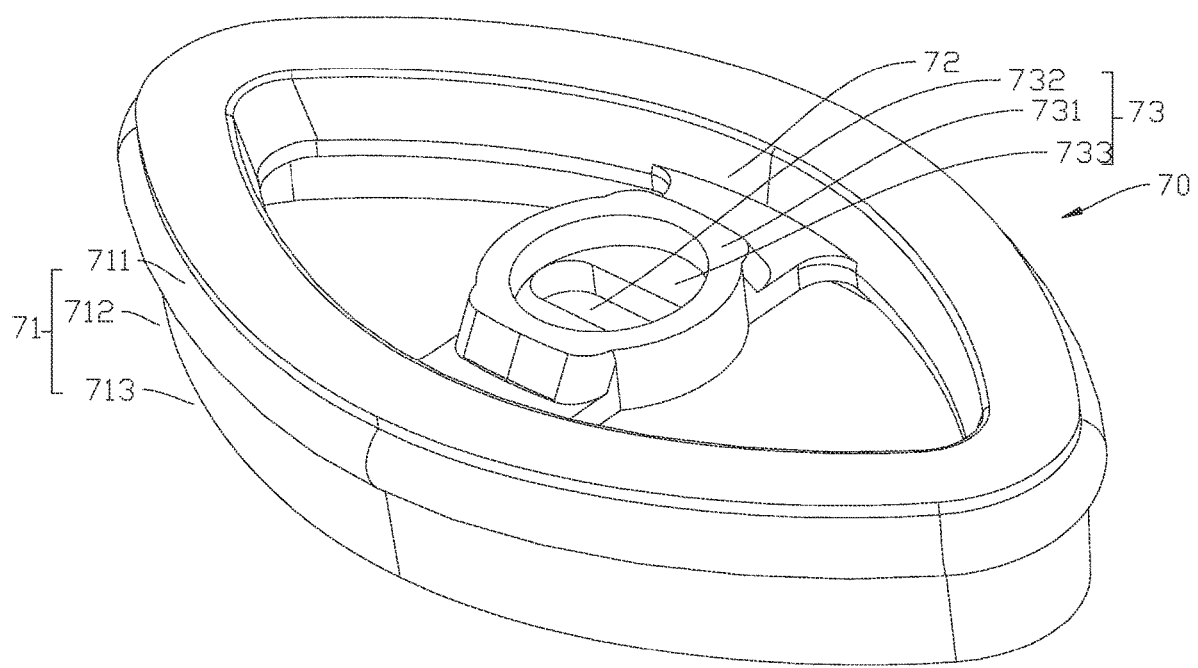
FIG. 13 is another perspective view of the sealing structure of the atomizer shown in FIG. 12.

As shown in FIG. 8, in some embodiments, the second conductive member 50 may be in a sheet shape, and may be laterally disposed on a surface of another one of the base 10 and the atomization assembly 30 facing one of the base 10 and the atomization assembly 30. In this embodiment, the second conductive member 50 may be disposed on the atomization assembly 30, and may be located on the atomizing surface 311 of the porous body 31. It can be understood that, in other embodiments, the second conductive member 50 may alternatively be disposed on a surface of the base 10 facing the atomizing surface 311. In other embodiments, the second conductive member 50 may not be limited to a sheet shape, but may be a dot shape or other shape.

In some embodiments, the number of the second conductive member 50 may be one or more second conductive members, which is not limited to two. In this embodiment, the two second conductive members 50 are spaced arranged at two opposite sides of the heating element 32 respectively, and are respectively electrically connected with the heating element 32. The two second conductive members 50 form an integral structure with the heating element 32, and can form straight sections of the heating element 32, and form an integral structure with the porous body 31 by sintering. The two second conductive members 50 can abut against the two first conductive members 40, respectively. Specifically, the two second conductive members 50 can abut against the abutting portions 43 of the first conductive members 40. During assembly of this embodiment, the base 10 with the first conductive member 40 is inserted into the sleeve, so that the first conductive members 40 respectively abut against the second conductive members 50 disposed on the porous body 31, so that alignment is not needed, the number of components and installation steps can be reduced, the production and assembly costs can be reduced, the automated assembly is facilitated, and the efficiency is improved. The second conductive member 50 may be made of silver, which can be in good contact with the first conductive member 40.

As shown in FIG. 3, FIG. 4, FIG. 10 and FIG. 11, in some embodiments, the sleeve includes a sleeve body 61, a cover body 62 and a limiting portion 63. The sleeve body 61 can be disposed on the base 10, and has an opening at one end facing the base 10, and may be used to receive the atomization assembly 30 and to define an atomizing chamber 132. The cover body 62 is disposed inside the sleeve body 61 and is integrally formed with the sleeve body 61, and may define a first receiving space for receiving the atomization assembly 30. The limiting portion 63 is disposed at an end of the sleeve body 61 away from the opening, and can be used for limiting the positon of the sealing structure 70 during assembly.

In some embodiments, a cross section of the sleeve body 61 may be elliptical, and includes a long axis and a short axis, the long axis is a symmetry axis of two opposite sides, and the short axis is a symmetry axis of another two opposite sides; the two opposite sides are respectively located on two opposite sides of the long axis, and the another two opposite sides are respectively located on two opposite sides of the short axis. The sleeve body 61 of this embodiment is disposed symmetrically with respect to a plane which is perpendicular to the cross section and where the long axis of the cross section is located, and is disposed symmetrically with respect to a plane which is perpendicular to the cross section and where the short axis of the cross section is located. Of course, it can be understood that in other embodiments, the cross-section of the sleeve body 61 may not be limited to an elliptical shape. The sleeve body 61 includes a top wall 611 and a side wall 612. The top wall 611 is disposed on an end surface of the sleeve body 61 away from the opening of the sleeve body 61, and the side wall 612 forms a sleeve portion for being sleeved on the base 10.

The sleeve body 61 is provided with a first through groove 613 and a second through groove 614 extending through two opposite sides of the sleeve body 61. The first through groove 613 can be disposed at an upper portion of the sleeve body 61, and can be configured for transferring out the airflow. The second through groove 614 can be disposed at a lower portion of the sleeve body 61 for allowing the airflow to pass therethrough. Outer wall surfaces of two opposite sides of the sleeve body 61 are respectively provided with air guide grooves 615. Two ends of the air guide groove 615 are respectively communicated with the first through groove 613 and the second through groove 614, and the air guide groove 615 can transfer the airflow from the second groove 614 to the first groove 613. The air guide groove 615 can be disposed on a surface of the cover body 62. By providing the first through groove 613, the second through groove 614 and the air guide groove 615 in the sleeve body 61, the sleeve body 61 can be easily demoulded, and an airflow passage can be defined.

In some embodiments, the sleeve body 61 is further provided with a third through groove 616 and a fourth through groove 617. The third through groove 616 and the fourth through groove 617 are respectively disposed at two sides of a central axis of the sleeve body 61, and the third through groove 616 and the fourth through groove 617 can extend through two opposite sides of the sleeve body 61, and extend through two side walls of the two opposite sides of the sleeve body, respectively. The third through groove 616 and the fourth through groove 617 can be respectively disposed at two corners of lower portions of two opposite sides of the sleeve body, and are communicated with a second receiving space 619 which is configured for receiving the base 10 and defined at a lower portion of the sleeve body 61. The third through groove 616 and the fourth through groove 617 form clamping positions 618 engaged with the base 10, so as to clamp the base 10, and be engaged with the hooks 131 on the supporting structure 13 of the base 10. In this embodiment, a first guide groove 6121 and a second guide groove 6122 are further provided on inner sides of the sleeve body 61. The first guide groove 6121 and the second guide groove 6122 can be formed by concave sidewalls of two opposite sides of the short axis toward the third through groove 616 and the fourth through groove 617 respectively, and can be used for guiding the base 10 during installation, specifically, for guiding the supporting structure 13 into the sleeve body 61. The first guide groove 6121 and the second guide groove 6122 are respectively communicated with the clamping positions 618. The third through groove 616 and the fourth through groove 617 can facilitate the demoulding of the sleeve body 61, facilitate the automatic production, facilitate the assembly of the atomizer, and facilitate the fixing of the base 10.

In some embodiments, the cover body 62 can be cuboid shaped, and is disposed between the first through groove 613 and the second through groove 614. A first receiving space 621 is defined at a lower side of the cover body 62, and can be used for receiving the atomization assembly 30. A liquid inlet hole 6211 may be defined in the first receiving space 621 to facilitate the liquid to enter the atomization assembly 30, and the liquid inlet hole 6211 may be adapted to the shape and dimension of the porous body 31. The liquid inlet hole 6211 is communicated with the porous body 31, which can facilitate the liquid to enter into the porous body 31. In this embodiment, the shape of the liquid inlet hole 6211 can be a bar shape, specifically, a rectangular shape. An isolator 622 may be disposed on a top portion of the cover body 62 to isolate the first receiving space 621 from the first groove 613. The isolator 622 may be formed by a top wall of the cover body 62. A bottom surface of the isolator 622 may be a curved surface, to facilitate the liquid inlet hole 6211 being communicated with a liquid hole 65 defined in the top wall 611 of the sleeve body 61.

In some embodiments, the top wall 611 of the sleeve body 61 is provided with an air outlet 63. The air outlet 63 is communicated with the first through groove 613, so as to output the airflow entering the first through groove 613 to the ventilation pipe 212. In this embodiment, the air outlet 63 can be disposed in a center of the top wall 611, and the air outlet 63 is communicated with the ventilation pipe 212 for outputting the aerosol to the ventilation pipe 212 for a user to suck.

In some embodiments, the top wall 611 is further provided with two liquid holes 64. The two liquid holes 64 and the air outlet 63 are disposed in a direction of the long axis of the top wall 611, and the two liquid holes 64 are respectively located at two sides of the air outlet 63. The two liquid holes 64 are respectively communicated with the first receiving space 621, specifically, communicated with the liquid inlet hole 6211, and upper portions of the two liquid holes 64 are communicated with the liquid storage cavity 211 for allowing the liquid in the liquid storage cavity 211 to flow to the porous body 31 on the first receiving space 621.

Referring to FIGS. 2 to 4 and FIGS. 12 to 13, the sealing structure 70 can be used for the atomizer 100, and can be arranged between the sleeve and the base 10, can be sleeved on the base 10, and can hermetically connect the sleeve, the base 10 and the cartridge 20. It can be understood that in other embodiments, the sealing structure 70 may not be limited to be used in the atomizer 100. In some embodiments, the sealing structure 70 may include an annular portion 71, at least one reinforcement portion 72, and a pickup portion 73. The annular portion 71 has elasticity and can be sleeved on the limiting boss 12 of the base 10. The at least one reinforcement portion 72 can be disposed in the annular portion 71, and two ends of the reinforcement portion 72 are respectively connected to two opposite sides of the annular portion 71. The at least one reinforcement portion 72 can be used to reinforce the rigidity of the annular portion 71 and reduce the deformation of the annular portion 71 when taking and placing the annular portion 71. The pickup portion 73 may be disposed inside the annular portion 71 and connected to the annular portion 71 through the reinforcement portion 72. The pickup portion 73 may be cooperated with a picker to facilitate the pick-up of the sealing structure 70.

In some embodiments, the annular portion 71 may be an elastic ring made of an elastic material, such as silicone or rubber, etc. In this embodiment, the annular portion 71 may be made of a silicone material. The shape of the annular portion 71 may be a circle or an ellipse or a square or a rectangle, and the shape thereof is fitted with the shape of the base 10. In this embodiment, the shape of the annular portion 71 is an ellipse. In this embodiment, the annular portion 71 may include a first sleeve portion 711, a second sleeve portion 713, and a sealing portion 712. The first sleeve portion 711 can be sleeved on the base 10. The sealing portion 712 is disposed between the first sleeve portion 711 and the second sleeve portion 713, and has an outer dimension larger than outer dimensions of the first sleeve portion 711 and the second sleeve portion 713. The sealing portion 712 can be used to seal a space between the base 10 and the cartridge 20. The second sleeve portion 713 may be disposed inside the sleeve and may be sleeved by the sleeve, and may seal a space between the sleeve and the base 10.

The at least one reinforcement portion 72 may include one or more reinforcement portion 72 and may be integrally formed with the annular portion 71. In some embodiments, the at least one reinforcement portion 72 may include at least two reinforcement portions 72. The at least two reinforcement portions 72 may be disposed separately and side by side, with two ends of each reinforcement portion being connected to two opposite sides of the annular portion 71 respectively. It can be understood that in other embodiments, the at least two reinforcement portions 72 may alternatively be arranged crosswise. In this embodiment, the at least one reinforcement portion 72 may include two reinforcement portions 72. The base 10 is provided with interference-preventing notches 19 to give place to the reinforcement portions 72, and the number and positions of the interference-preventing notches 19 are matched with those of the reinforcement portions 72, so as to facilitate the installation of the sealing structure 70. In some embodiments, the reinforcement portion 72 may be a strip or a sheet, and in this embodiment, the reinforcement portion 72 may be a sheet shaped reinforcement rib.

In some embodiments, the pickup portion 73 may be disposed between the two reinforcement portions 72, side walls of the pickup portion 73 may be respectively connected with the reinforcement portions 72, and the pickup portion 73 may be integrally formed with the reinforcement portions 72. In this embodiment, the pickup portion 73 can be disposed at an outlet end of the air inlet passage 14, and includes a cylindrical body 731 and at least one pickup hole 732. The cylindrical body 731 may be disposed in the air inlet passage 14, and may be used to converge the airflow. The at least one pickup hole 732 may be provided in the cylindrical body 731, and may cooperate with a picker to facilitate the pickup by the picker.

The inside of the cylindrical body 731 may define a collecting cativy for converging the airflow and reducing the liquid leakage, preventing the airflow in the air inlet passage 14 from escaping, and outputting the airflow through the pickup hole 732. In this embodiment, the cylindrical body 731 may be a cylinder whose diameter is matched with the diameter of the air inlet passage 14.

The at least one pickup hole 732 may include one or more pickup holes 732, and in this embodiment includes one pickup hole 732. The at least one pickup hole 732 is communicated with the air inlet passage 14, and may form an outlet hole of the air inlet passage 14 for outputting the airflow into the atomizing chamber 132. In this embodiment, the pickup hole 732 can be a strip-shaped hole, and can be disposed along the long axis of the annular portion 71 and extend toward the long axis of the annular portion 71. The pickup hole 732 can increase the contact area between the airflow and the atomizing surface 311, so as to facilitate the atomization of the atomization assembly 30. An isolation portion 733 is provided between an outer periphery of the strip-shaped hole and an inner side wall of the cylindrical body 731 so as to prevent liquid from leaking directly from the pickup hole. Of course, it can be understood that in other embodiments, the pickup hole 732 may not be limited to a strip-shaped hole. When the atomizer is assembled by an automatic assembling method, the picker can be inserted into the pickup hole 732 of the sealing structure 70 to form an interference fit with the pickup portion 73, and then the sealing structure is taken to the base 10 of the atomizer. In other embodiments, the pickup holes 732 may be two or more, and the picker may be a holder which may be inserted into any two of the pickup holes 732 to clamp the annular portion 71.

As shown in FIGS. 2 to 4 and FIGS. 14 to 15, the elastic member 80 can be disposed on a side of the porous body 31 away from the base 10, and has one end abutting against a top wall of the cover body 62 of the housing, and another end abutting against the porous body 31. The elastic member 80 can be used to prevent the porous body from being crushed, and meanwhile, can serve as a buffer to facilitate good contact between the first conductive member 40 and the second conductive member 50 on the porous body 31. In this embodiment, specifically, one end of the elastic member 80 may abut against an end surface of an inner side of the cover body 62 which is located on an outer periphery of the liquid inlet hole 6211, and another end of the elastic member 80 may abut against an end surface of the porous body 31 which is located on an outer periphery of the liquid adsorbing groove 312.

In some embodiments, the elastic member 80 can be an elastic ring or an elastic sheet, and in this embodiment, the elastic member 80 is the elastic ring. A telescopic amount of the elastic member 80 is fitted with the difference between a height of a free end of each first conductive member 40 extending toward the atomization assembly 30 and a height of the atomizing chamber 132, so that the first conductive member 40 and the second conductive member 50 can be in good contact with each other. In this embodiment, the telescopic amount of the elastic member 80 may be 0.5 to 0.8 mm.

In this embodiment, a sealing assembly 90 is further disposed between the sleeve and the cartridge 20. The sealing assembly 90 may be used to seal a space between the cartridge 20 and the sleeve. The sealing assembly 90 can be a conventional sealing ring, of course, it can alternatively be the sealing structure 70 of the present disclosure, and in this embodiment, specifically, it is the sealing structure 70 of the present disclosure. The annular portion 71 of the sealing structure 70 may be sleeved on the sleeve, and the sleeve is provided with a limiting boss sleeved by the sealing assembly 90.

An automated atomizer assembling method 100 in some embodiments may include the following steps:

Inserting a picker from the pickup hole 732 of the pickup portion 73 of the sealing structure 70, taking the sealing structure 70 to the base 10 of the atomizer 100, and sleeving one end of the annular portion 71 of the sealing structure on the outer periphery of the base 10. Specifically, mounting a pressing plate on the picker, driving the picker to descend, inserting the picker into the pickup hole 732 to form a interference fit with the pickup hole 732, and driving the picker to ascend and descend, placing the sealing structure 70 on the base 10 by passing through the supporting structure 13 of the base 10, and then driving the pressing plate on the picker to press down, so that the first sleeve portion 711 of the annular portion 73 is sleeved on the limiting boss 12 of the base 10.

Mounting the atomization assembly 30 into the atomization housing 60, and inserting the base 10 assembled with the sealing structure 70 into the atomization housing 60, and sleeving the atomization housing 60 on another end of the annular portion 71 of the sealing structure 70. Specifically, firstly inserting the elastic member 80 into the sleeve, then abutting one end of the atomization assembly 30 installed in the sleeve against the elastic member 80, and then inserting the supporting structure 13 of the base 10 into the sleeve along the guide groove in the inner side of the sleeve to support the atomization assembly 30, and buckling the hooks 131 on two sides of the supporting structure 13 to the clamping positions 618 of the sleeve. Finally, sleeving the sealing assembly 90 on the end of the sleeve away from the base 10.

Mounting the base 10, the atomization housing 60, the sealing structure 70, and the atomization assembly 30 into the cartridge 20. Specifically, inserting the assembled components such as the base 10, the atomization housing 60, the sealing structure 70 and the atomization assembly 30 into the cartridge 20, and buckling the buckles 111 on two sides of the base 10 into the buckling grooves 213 of the cartridge 20.

FIGS. 16 and 17 show a preferred embodiment of the electronic atomization device of the present disclosure. The electronic atomization device includes a power supply device 200 and an atomizer 100. The power supply device 200 can be connected to the first conductive member 40 of the base 10. The power supply device 200 includes a shell, a power supply assembly and a control assembly which are disposed in the shell. A positive pole and a negative pole of the power supply assembly can be respectively abutted with the transverse connecting portions of the two first conductive members 40 on the base 10. The control assembly, which can be a pneumatic control switch or a manual control switch, is able to control the power supply assembly to supply power to the atomizer 100.

It should be understandable that the above embodiments are only preferred embodiments of the disclosure, and the description thereof is more specific and detailed, but it is not to be construed as limiting the scope of the patent of the disclosure. It should be noted that a person skilled in the art can freely combine the foregoing technical features and also can make several modifications and improvements without departing from the concept of the disclosure, and these modifications and improvements are all within the scope of protection of the present disclosure. Therefore, all equivalent transformations and modifications made according to the scope of the claims of the disclosure shall fall within the scope of the claims of the disclosure.

What is claimed is:

1. A sealing structure for an atomizer, comprising an elastic annular portion (71) and at least one reinforcement portion (72); wherein the at least one reinforcement portion (72) is disposed in the annular portion (71), and two ends of the at least one reinforcement portion (72) are connected to two opposite sides of the annular portion (71) respectively to thereby reinforce the rigidity of the annular portion (71) and reduce deformation of the annular portion (71) during a process of taking or placing the sealing structure;

wherein the sealing structure further comprises a pickup portion (73); and the pickup portion (73) is disposed on an inner side of the annular portion (71) and is connected with the annular portion (71) through the at least one reinforcement portion (72);

the pickup portion (73) comprises a cylindrical body (731) and at least one pickup hole (732) configured to allow a picker to extend thereinto for lifting the sealing structure; and the at least one pickup hole (732) comprises a strip-shaped hole which is defined in the cylindrical body (731); and an isolation portion (733) is arranged between the periphery of the pickup hole (732) and an inner side wall of the cylindrical body (731);

a collecting cavity is defined inside the cylindrical body (731) and located at an upstream of the at least one pickup hole (732) for converging airflow and outputting the airflow through the pickup hole (732);

wherein the at least one pickup hole (732) has an axial size less than that of the annular portion (71) and the isolation portion (733) acts as an axial end of the collecting cavity;

wherein the strip-shaped hole defines a long axis direction and a short axis direction;

the isolation portion (733) extends outwardly from the periphery of the strip-shaped hole to the inner side wall of the cylindrical body (731); and the annular portion (71) has an elliptical shape; the strip-shaped hole is disposed in a long axis direction of the annular portion (71) and the long axis direction of the strip-shaped hole extends in the long axis direction of the annular portion (71);

wherein the at least one reinforcement portion (72) comprises at least two reinforcement portions (72) connected to an outer side of the cylindrical body (731), and the at least two reinforcement portions (72) are located on opposite sides of the strip-shaped hole in the short axis direction of the strip-shaped hole and connected with parts of the annular portion (71) in a short axis direction of the annular portion (71);

wherein two through openings are formed between the cylindrical body (731) and the annular portion (71) and respectively located on opposite sides of the strip-shaped hole in the long axis direction of the strip-shaped hole.

2. The sealing structure for an atomizer according to claim 1, wherein the at least one pickup hole (732) is configured to form an interference fit with the picker.

3. The sealing structure for an atomizer according to claim 2, wherein the at least one pickup hole (732) is located between two opposite axial ends of the annular portion (71); the cylindrical body (731) comprises two opposite axial ends, an opening of the at least one pickup hole (732)

is defined at one of the two opposite axial ends of the cylindrical body (731) which is flush with an axial end surface of the at least one reinforcement portions (72); and another one of the two opposite axial ends of the cylindrical body (731) extends in a direction away from the at least one pickup hole (732).

4. The sealing structure for an atomizer according to claim 2, wherein the annular portion (71) comprises a first sleeve portion (711), a second sleeve portion (713) and a sealing portion (712);

the sealing portion (712) is disposed between the first sleeve portion (711) and the second sleeving portion (713) in an axial direction of the annular portion (71);

the sealing portion (712) has an outer dimeter greater than those of the first sleeve portion (711) and the second sleeving portion (713) for sealing a space;

a flange extends inwardly from an inner side wall of the annular portion (71); and the ends of the at least two reinforcement portions (72) away from the pickup portion (73) are connected with the flange.

5. The sealing structure for an atomizer according to claim 1, wherein the isolation portion (733) is configured for preventing liquid from leaking directly from the at least one pickup hole.

6. The sealing structure for an atomizer according to claim 5, wherein a pair of said isolation portions (733) is arranged, and each of the pair of said isolation portions (733) extends from one of opposite two sides of the strip-shaped hole to the inner side wall of the cylindrical body (731) in the short axis direction of the strip-shaped hole.

7. An atomizer, comprising a base (10), a cartridge (20) sleeved on a periphery of the base (10), an atomization assembly (30) disposed in the cartridge (20), and a sealing structure (70); wherein, the sealing structure (70) is sleeved on the base (10) and disposed between the base (10) and the cartridge (20); the sealing structure (70) comprises an elastic annular portion (71) and at least one reinforcement portion (72); the at least one reinforcement portion (72) is disposed in the annular portion (71), and two ends of the at least one reinforcement portion (72) are connected to two opposite sides of the annular portion (71) respectively;

wherein the sealing structure further comprises a pickup portion (73) configured to cooperate with a picker to allow the sealing structure to be picked up by the picker;

the pickup portion (73) is disposed on an inner side of the annular portion (71) and is connected with the annular portion (71) through the at least one reinforcement portion (72);

the annular portion (71) of the sealing structure is sleeved on the base (10) and is located between the base (10) and the cartridge (20);

the base (10) comprises a base body (11), and the base body (11) is provided with an air inlet passage (14);

the pickup portion (73) is disposed at an outlet end of the air inlet passage (14);

the pickup portion (73) comprises a cylindrical body (731), a strip-shaped pickup hole (732) defined in the cylindrical body (731) and configured to allow the picker to extend thereinto for lifting the sealing structure, and an isolation portion (733);

a shape and a dimension of the cylindrical body (731) are matched with a shape and a dimension of the air inlet passage (14);

the pickup hole (732) is communicated with the air inlet passage (14) to form an air outlet hole to allow air to enter an atomizing chamber (132) of the atomization assembly (30) after passing through the air inlet passage (14) and the pickup hole (732) in sequence;

the at least one reinforcement portion (72) comprises at least two reinforcement portions (72) connected to an outer side of the cylindrical body (731) and respectively located on opposite sides of the strip-shaped hole in a short axis direction of the strip-shaped hole; and the isolation portion (733) of the pickup portion (73) is arranged between the periphery of the strip-shaped hole and the inner side wall of the cylindrical body (731) and extends outwardly from a periphery of the strip-shaped hole to an inner side wall of the cylindrical body (731); and wherein the elastic annular portion (71), the at least one reinforcement portion (72) and the pickup portion (73) of the sealing structure (70) are integrally formed as an integral structure; and wherein a pair of through openings is formed between the cylindrical body (731) and the annular portion (71) and respectively located on opposite sides of the strip-shaped hole in a long axis direction of the strip-shaped hole.

8. The atomizer according to claim 7, wherein the atomizer further comprises an atomization housing (60) disposed on the base (10); and the atomization housing (60) comprises a sleeve;

the sealing structure is disposed between the base (10) and the sleeve; and the annular portion (71) comprises a first sleeve portion (711), a second sleeve portion (713) and a sealing portion (712); the first sleeve portion (711) is sleeved on the base (10); the second sleeve portion (713) is disposed at an inner side of the sleeve for sleeving the sleeve; the sealing portion (712) is disposed between the first sleeve portion (711) and the second sleeving portion (713) to seal a space between the base (10) and the cartridge (20).

9. The atomizer according to claim 8, wherein an outer dimension of the sealing portion (712) is larger than outer dimensions of the first sleeve portion (711) and the second sleeve portion (713).

10. The atomizer according to claim 8, wherein a liquid storage cavity (211) is defined inside the cartridge (20); the sealing structure is disposed between the sleeve and the liquid storage cavity (211); and the annular portion (71) of the sealing structure is sleeved on an outer periphery of the sleeve.

11. The atomizer according to claim 7, wherein the atomization assembly (30) comprises a porous body (31) and a heating element (32), the heating element (32) is disposed on a side of the porous body (31) facing the base (10);

wherein the strip-shaped hole and the heating element (32) are disposed facing each other in an axial direction of the cylindrical body (731).

12. The atomizer according to claim 11, wherein the heating element (32) is elongated and disposed along a length direction of the porous body (31), and the long axis direction of the strip-shaped hole is parallel to the length direction of the porous body (31) and an overall length direction of the heating element (32).

13. The atomizer according to claim 7, wherein the base (10) further comprises two support columns (13*a*) provided on the base body (11), and the air inlet passage (14) is located in the middle of the two support columns (13*a*);

the at least one reinforcement portion (72) is sunken with respect to the annular portion (71) in an axial direction of the annular portion (71) to thereby form a chamber therebetween; and the pair of through openings and the chamber are distributed in the axial direction of the the annular portion (71) and communicated with each other such that each of the two support columns (13*a*) of the base (10) is capable of being inserted into one of the axial through openings and the chamber in sequence.

14. The atomizer according to claim 7, wherein a collecting cavity is defined inside the cylindrical body (731) of the pickup portion (73) of the sealing structure (70) for converging airflow and outputting the airflow through the pickup hole (732); and the collecting cavity is located between the outlet end of the air inlet passage (14) and the pickup hole (732); and an area of the collecting cavity in a cross-section perpendicular to the axis of the cylindrical body (731) is greater than an area of the at least one pickup hole (732) in a cross-section perpendicular to the axis of the cylindrical body (731).

15. The atomizer according to claim 14, wherein the collecting cavity and the outlet end of the air inlet passage (14) are disposed opposite to each other in an axial direction of the cylindrical body (731), and a number of screens (18) are provided internally at the outlet end of the air inlet passage (14) to prevent liquid leakage from the air inlet passage (14); and wherein a plurality of holes provided in the number of screens (18) are configured to form liquid films when liquid drips onto the number of screens (18) to prevent liquid leakage.

16. An electronic atomization device comprising a power supply device and an atomizer, the atomizer comprising a base (10), a cartridge (20) sleeved on a periphery of the base (10), an atomization assembly (30) disposed in the cartridge (20), and a sealing structure (70); wherein, the sealing structure (70) is sleeved on the base (10) and disposed between the base (10) and the cartridge (20);

the sealing structure (70) comprises an elastic annular portion (71) and at least one reinforcement portion (72); the at least one reinforcement portion (72) is disposed in the annular portion (71), and two ends of the at least one reinforcement portion (72) are connected to two opposite sides of the annular portion (71) respectively;

wherein the sealing structure further comprises a pickup portion (73) configured to cooperate with a picker to allow the sealing structure to be picked up by the picker; and the pickup portion (73) is disposed on an inner side of the annular portion (71) and is connected with the annular portion (71) through the reinforcement portion (72);

the annular portion (71) of the sealing structure is sleeved on the base (10) and is located between the base (10) and the cartridge (20);

the base (10) comprises a base body (11); and the base body (11) is provided with an air inlet passage (14);

the pickup portion (73) is disposed at an outlet end of the air inlet passage (14);

the pickup portion (73) comprises a cylindrical body (731) and a strip-shaped pickup hole (732) which is defined in the cylindrical body (731) and communicated with the air inlet passage (14) to allow air to enter an atomizing chamber (132) of the atomization assembly (30) after passing through the air inlet passage (14) and the strip-shaped pickup hole (732) in sequence;

the sealing structure (70) further comprises a pair of axial through openings disposed on opposite sides of the reinforcement portion (72) in a long axis direction of the strip-shaped hole, and the base (10) comprises two support columns (13*a*) being inserted into the axial through openings respectively; and the at least one reinforcement portion (72) comprises at least two reinforcement portions (72) connected to an outer side of the cylindrical body (731) and located on opposite sides of the strip-shaped hole in a short axis direction thereof.

17. The electronic atomization device according to claim 16, wherein the annular portion (71), the at least one reinforcement portion (72) and the pickup portion (73) of the sealing structure (70) are integrally formed;

a shape and a dimension of the cylindrical body (731) are matched with a shape and a dimension of the air inlet passage (14); and the pickup hole (732) is communicated with the air inlet passage (14) to form an air outlet hole.

18. The electronic atomization device according to claim 16, wherein the atomizer further comprises an atomization housing (60) disposed on the base (10); and the atomization housing (60) comprises a sleeve;

the sealing structure is disposed between the base (10) and the sleeve; and the annular portion (71) comprises a first sleeve portion (711), a second sleeve portion (713) and a sealing portion (712); the first sleeve portion (711) is sleeved on the base (10); the second sleeve portion (713) is disposed at an outside side of the sleeve for sleeving the sleeve; the sealing portion (712) is disposed between the first sleeve portion (711) and the second sleeving portion (713) to seal a space between the base (10) and the cartridge (20).

19. The sealing structure for an atomizer according to claim 16, wherein two first conductive members (40) are spacedly disposed on the base 11, and two second conductive members (50) are spacedly disposed on the atomization assembly (30) and abutted with the two first conductive members (40) respectively so as to form a conductive connection therebetween.

* * * * *